(12) United States Patent
Abdelghani (10) Patent No.: US 9,421,476 B2
(45) Date of Patent: Aug. 23, 2016

(54) DISTILLATION PROCESS AND MULTI-COLUMN HEAT-INTEGRATED DISTILLATION SYSTEM

(75) Inventor: Mohamed Sabri Abdelghani, Riyadh (SA)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 730 days.

(21) Appl. No.: 13/641,979

(22) PCT Filed: Apr. 18, 2011

(86) PCT No.: PCT/EP2011/001951
§ 371 (c)(1),
(2), (4) Date: Oct. 18, 2012

(87) PCT Pub. No.: WO2011/131325
PCT Pub. Date: Oct. 27, 2011

(65) Prior Publication Data
US 2013/0037404 A1 Feb. 14, 2013

(30) Foreign Application Priority Data
Apr. 21, 2010 (EP) .................................... 10075162

(51) Int. Cl.
*B01D 3/14* (2006.01)
*B01D 3/42* (2006.01)
*B01D 3/00* (2006.01)
(Continued)

(52) U.S. Cl.
CPC ................ *B01D 3/143* (2013.01); *B01D 3/007* (2013.01); *B01D 3/322* (2013.01); *B01D 3/42* (2013.01); *C07C 7/04* (2013.01); *B01D 3/4283* (2013.01); *B01D 3/4288* (2013.01); *B01D 3/4294* (2013.01); *Y02P 20/124* (2015.11); *Y02P 20/57* (2015.11)

(58) Field of Classification Search
CPC ... B01D 3/4288; B01D 3/4283; B01D 3/4294
See application file for complete search history.

(56) References Cited

U.S. PATENT DOCUMENTS 3,402,124 A * 9/1968 Jones ............................ 208/353
4,110,374 A * 8/1978 Inoue .................... C07C 273/04
564/71
4,162,198 A 7/1979 Stockburger et al.
(Continued)

OTHER PUBLICATIONS

Extended European Search Report; European Application No. 10075162.7; Date of Mailing: Sep. 30, 2010; 6 Pages.
(Continued)

*Primary Examiner* — Renee E Robinson
*Assistant Examiner* — Jonathan Pilcher
(74) *Attorney, Agent, or Firm* — Cantor Colburn LLP (57) ABSTRACT

A distillation system and process for separating a multi-component feed mixture in a distillation system comprising a first distillation column having a first fired reboiler, and at least a second distillation column having a second heat-exchange reboiler, comprising the steps of a) introducing the feed mixture to the first column, and separating into at least a first top and a first bottom product; b) taking part of the first bottom product for providing heat to the second reboiler as a utility stream; and c) feeding part of said utility stream after heat-exchange as main feed to the second column for further separation. This process allows significant energy savings, by reduction of the amount of external heat required for the fired reboiler and omission of a conventionally used heat-exchanger.

14 Claims, 6 Drawing Sheets

(51) Int. Cl.
*B01D 3/32* (2006.01)
*C07C 7/04* (2006.01)

(56) References Cited

U.S. PATENT DOCUMENTS

| | | | |
|---|---|---|---|
| 4,464,190 A | | 8/1984 | Gulsby |
| 5,457,277 A | * | 10/1995 | Sy .............................. 202/154 |
| 5,554,264 A | | 9/1996 | Sy |
| 2002/0016520 A1 | * | 2/2002 | Paggini et al. ................ 585/323 |
| 2010/0197987 A1 | * | 8/2010 | Almering ...................... 585/671 |

OTHER PUBLICATIONS

International Search Report; International Application No. PCT/EP2011/001951; International Filing Date: Apr. 18, 2011; Date of Mailing: Sep. 26, 2011; 4 Pages.

Written Opinion of the International Searching Authority; International Application No. PCT/EP2011/001951; International Filing Date: Apr. 18, 2011; Date of Mailing: Sep. 26, 2011; 5 Pages.

\* cited by examiner

DISTILLATION PROCESS AND MULTI-COLUMN HEAT-INTEGRATED DISTILLATION SYSTEM

This application is a 371 of International Application No. PCT/EP2011/001951, filed Apr. 18, 2011, which claims priority to European Application No. 10075162.7, filed Apr. 21, 2010, both of which are hereby incorporated by reference in its entirety.

The invention relates to a process for separating a multi-component feed mixture in a distillation system comprising at least two distillation columns each having a reboiler system. More specifically, the invention relates to a process for separating a multi-component feed mixture in a distillation system comprising a first distillation column having a first fired reboiler, and at least a second distillation column having a second heat-exchange reboiler.

The invention also relates to such distillation system comprising a first distillation column having a first fired reboiler, and at least a second distillation column having a second heat-exchange reboiler, which system is suitable for separating a multi-component mixture with the process of the invention.

Distillation is one of the most widely used separation techniques in the chemical industry. Standard distillation methods typically introduce a multi-component feed—that is a mixture of two or more miscible components having different boiling points—to a distillation column, apply heat at the bottom of the column and cool at the top. The different components in the feed will therefore separate according to their respective boiling points between the top and bottom of the column. Top and bottom, and optionally other intermediate products are thus obtained. The specifications of the separated products can be controlled by operating parameters like pressure, temperatures, and flow rates in addition to column internal design and size. The feed temperature to a column is always lower than the bottom temperature of that column, and may be controlled by a heat exchanger. Of particular interest is the supply of heat to the bottom of the column and to the feed, especially in case of component mixtures that have relatively high boiling points, e.g. higher hydrocarbons and aromatics. Basically, distillation only requires energy in the form of heat as external input. Heat is typically supplied to circulating bottom product using a heat-exchanger type of reboiler unit, wherein steam is applied on one side-usually called the utility side—where it transfers heat to the column liquid bottom product on the other side of the heat exchanger—usually called the process side-, after which heated bottom product is returned to the column. In case the column requires significant heat input to heat up the bottom liquid to the required temperature, high pressure steam may be used. Such steam source may however not be available at the plant, may be costly to produce, or may not have sufficient heat capacity to heat the bottom circulating product to the required temperature. Alternatively, the heat can be supplied to the utility side by a hot oil stream, which is heated by a fired heater. Such fired heater can supply hot oil stream to more than one column bottom via their heat-exchange reboilers.

Such separation process and distillation system are known from inter alia U.S. Pat. No. 5,457,277A and U.S. Pat. No. 5,554,264A. These publications disclose a process for separating a multi-component feed mixture in a distillation system comprising a first distillation column having a first bottom outlet and a first fired reboiler, and at least a second distillation column having a second bottom outlet and a second heat-exchange reboiler, comprising the steps of i) Introducing the feed mixture to the first column, and separating into at least a first top and a first bottom product;
ii) Feeding part of the first bottom product from the first bottom outlet as main feed to the second column;
iii) Heating the other part of the first bottom product in the first reboiler and returning to the first column as a first circulating reboiler stream; and
iv) Taking part of the first circulating reboiler stream to provide heat to the second reboiler as a utility stream, and recombining said utility stream after heat-exchange with said first circulating reboiler stream and returning to the first column.

Optionally, said part of the first circulating reboiler stream having provided heat to the second reboiler may be partly used as an additional feed to the second column. This is possible, as the first circulating reboiler stream is of temperature higher than is required as feed temperature to the second distillation column.

This process advantageously applies only one fired circulating reboiler, and uses part of the heated first bottom product as a utility stream to supply heat to heat-exchange type of reboiler(s) of downstream column(s), and then mainly recycles it to the first column. Prior art processes used either multiple fired reboilers, or a separate hot oil system, which is less energy efficient and/or more expensive than applying said multi-column heat-integrated distillation system.

There is, however, always a need in industry to further improve the energy efficiency of a process.

It is the object of the present invention to provide a highly energy-efficient multi-column distillation process.

This objective is reached according to the invention with a process for separating a multi-component feed mixture in a distillation system comprising a first distillation column having first fired reboiler, and at least a second distillation column having a second heat-exchange reboiler, comprising the steps of a) Introducing the feed mixture to the first column, and separating into at least a first top and a first bottom product;
b) Taking part of the first bottom product for providing heat to the second reboiler as a utility stream;
c) Feeding part of said utility stream after heat-exchange as main feed to the second column for further separation.

The process according to the invention uses the product from the bottom of the first column to indirectly heat the second column as a utility stream via its heat-exchange reboiler, and is subsequently also used as—preferably single—feed stream of the second column; this way significantly reducing the amount of external heat required for the fired reboiler, thus making the process more energy efficient.

Further, in the process pressure and temperature of the feed stream to the second column may be adiabatically adjusted, omitting a conventionally used heat-exhanger and further preventing loss of energy. The resulting reduced fuel gas usage of the process will also reduce overall plant $CO_2$ emissions. Accordingly, both temperature and pressure of said part of said utility stream after heat-exchange may be adiabatically adjusted before feeding to the second column. Preferably, the temperature and pressure of said part of said utility stream after heat-exchange are adiabatically adjusted by passing the stream through means for adiabatically adjusting pressure and temperature, most preferably through an expansion valve.

In the process according to the invention the first bottom product used as a utility stream is typically of higher temperature than the required feed temperature for the second column. Preferably, the temperature of said utility stream is about 60, 70, 80 or even 90° C. higher than the required second column feed temperature.

In step c) of the process according to the invention main feed means that this is the dominant feed to the column. Preferably, this stream constitutes at least 70 vol % of the total feed mixture to be separated, more preferably it forms at least 80, 90, or 95 vol % of the total feed. Most preferably, said part of said utility stream after heat-exchange is the single feed stream to the second column.

The process according to the invention may comprise a further step of feeding the other part of said utility stream after heat-exchange to the first reboiler, where it is heated and re-used in the process.

In the process according to the invention, adjusting pressure, temperature, and/or flow-rate of the combined utility/feed stream can be used to further optimize energy efficiency. For example, by adjusting pressure and temperature a major part of the utility stream after heat-exchange can be used as feed to the second column, thus minimizing the excess that is to be returned and heated in the first reboiler. The skilled man knows how to control or change processing conditions in the process. The pressure of a stream is preferably adjusted with a variable pressure pump or with a letdown pressure valve. Temperature of a stream can be changed via indirect heat-exchange with a stream of different temperature available in the process, or by mixing streams of different temperature. Preferably, both temperature and pressure are adjusted by passing a stream through means for adiabatically adjusting pressure and temperature, for example an expansion valve.

In a preferred way of operating, the process according to the invention comprises the steps of
a) Introducing the feed mixture into the first column, and separating into at least a first top and a first bottom product;
b) Taking part of the first bottom product for providing heat to the second reboiler as a utility stream;
c) Feeding part of said utility stream after heat-exchange as main feed to the second column for further separation;
d) Combining other part of said utility stream after heat-exchange with the other part of the first bottom product, heating in the first reboiler and returning to the first column as a first circulating reboiler stream.

Preferably, in step b) of this process the pressure of first bottom product is adjusted before providing heat to the second reboiler.

The process preferably further comprises a step wherein part of the heated stream from the first reboiler is added to the utility stream in step b) to adjust temperature of said stream.

In the process according to the invention both temperature and pressure of said part of said utility stream after heat-exchange may be adiabatically adjusted before feeding to the second column. Preferably, the temperature and pressure of said part of said utility stream after heat-exchange are adiabatically adjusted by passing the stream through means for adiabatically adjusting pressure and temperature, most preferably through an expansion valve.

In a further preferred way of operating, the process according to the invention comprises the steps of
a) Introducing the feed mixture into the first column, and separating into at least a first top and a first bottom product;
b) Heating the first bottom product in the first reboiler and returning part thereof to the first column as a first circulating reboiler stream;
c) Taking the other part of heated stream from the first reboiler for providing heat to the second reboiler as a utility stream,
d) Feeding part of said utility stream after heat-exchange as main feed to the second column for further separation;
e) Heating other part of said utility stream after heat-exchange with the first bottom product in step b).

Preferably in this process step b) comprises first adjusting pressure of the first bottom product, and then heating in the reboiler.

In the process according to the invention both temperature and pressure of said part of said utility stream after heat-exchange may be adiabatically adjusted before feeding to the second column. Preferably, the temperature and pressure of said part of said utility stream after heat-exchange are adiabatically adjusted by passing the stream through means for adiabatically adjusting pressure and temperature, most preferably through an expansion valve.

Preferably the process of invention further comprises a step of taking part of second bottom product, heating in the second reboiler and returning to the second column as a second circulating reboiler stream.

The process according to the invention can also comprise three or more columns, each having its heat-exchange reboiler and circulating reboiler stream, and similar as described above for the second column; depending on the composition of the feed stream and number of components to be separated.

In the process according to the invention the feed mixture is preferably a mixture of components with relatively high boiling points, which requires substantial amounts of energy to be added to the distillation process, especially via the fired reboiler. Preferably, the feed mixture comprises hydrocarbons with boiling points higher than 100° C.; more preferably a mixture of aromatic hydrocarbons. Preferably, in the process according to the invention the hydrocarbons used as feed to second column have a boiling range of about 145 to 280° C.

In a specifically preferred embodiment the process according to the invention uses a feed mixture comprising aromatic hydrocarbons with 8 or more carbon atoms (C8+ aromatics). Such a mixture for example is produced in an aromatics plant for production of benzene, toluene and xylenes (abbreviated as BTX). The process preferably relates to separating such C8+ mixture into xylenes ($C_8H_{10}$ isomers) and C9+ in a first column, and further separating the C9+ bottom product into a C9 and C10 overhead and C10+ bottom fraction (comprising di-aromatic compounds like naphthalene).

Figure 1:
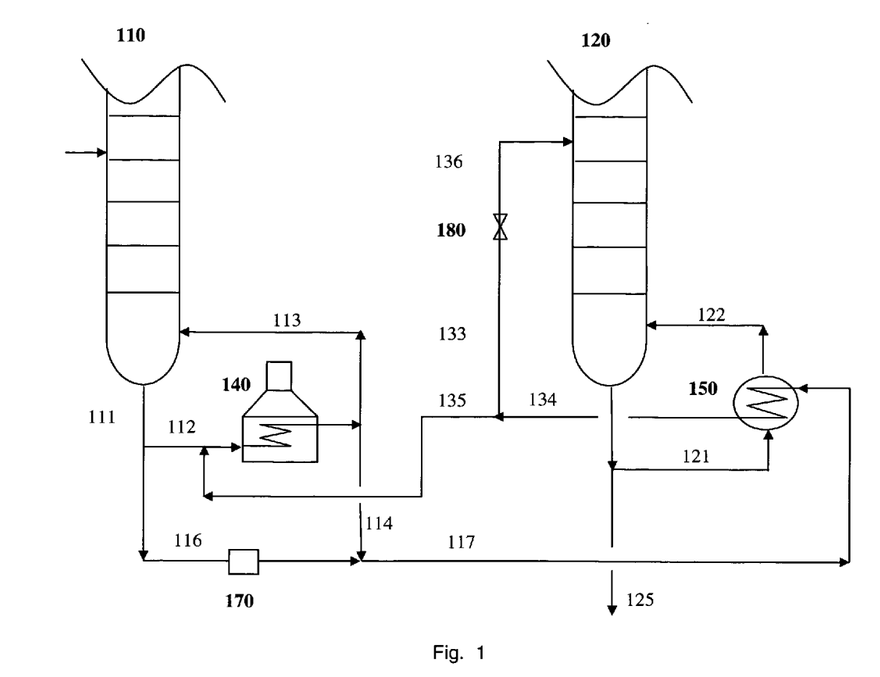
FIG. 1 is a schematic depiction of an example of a two-column distillation process.
Figure 2:
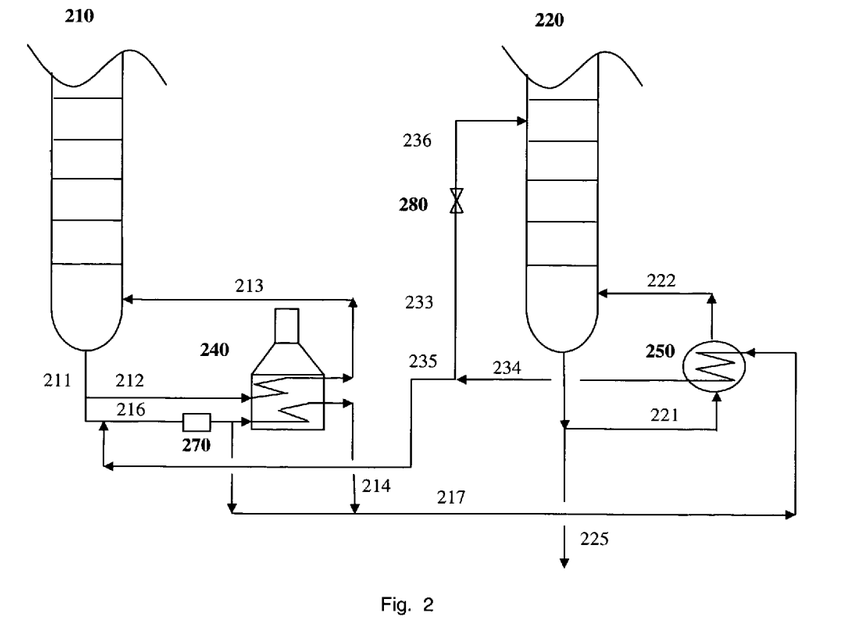
FIG. 2 is a schematic depiction of another example of a two-column distillation process.
Figure 3:
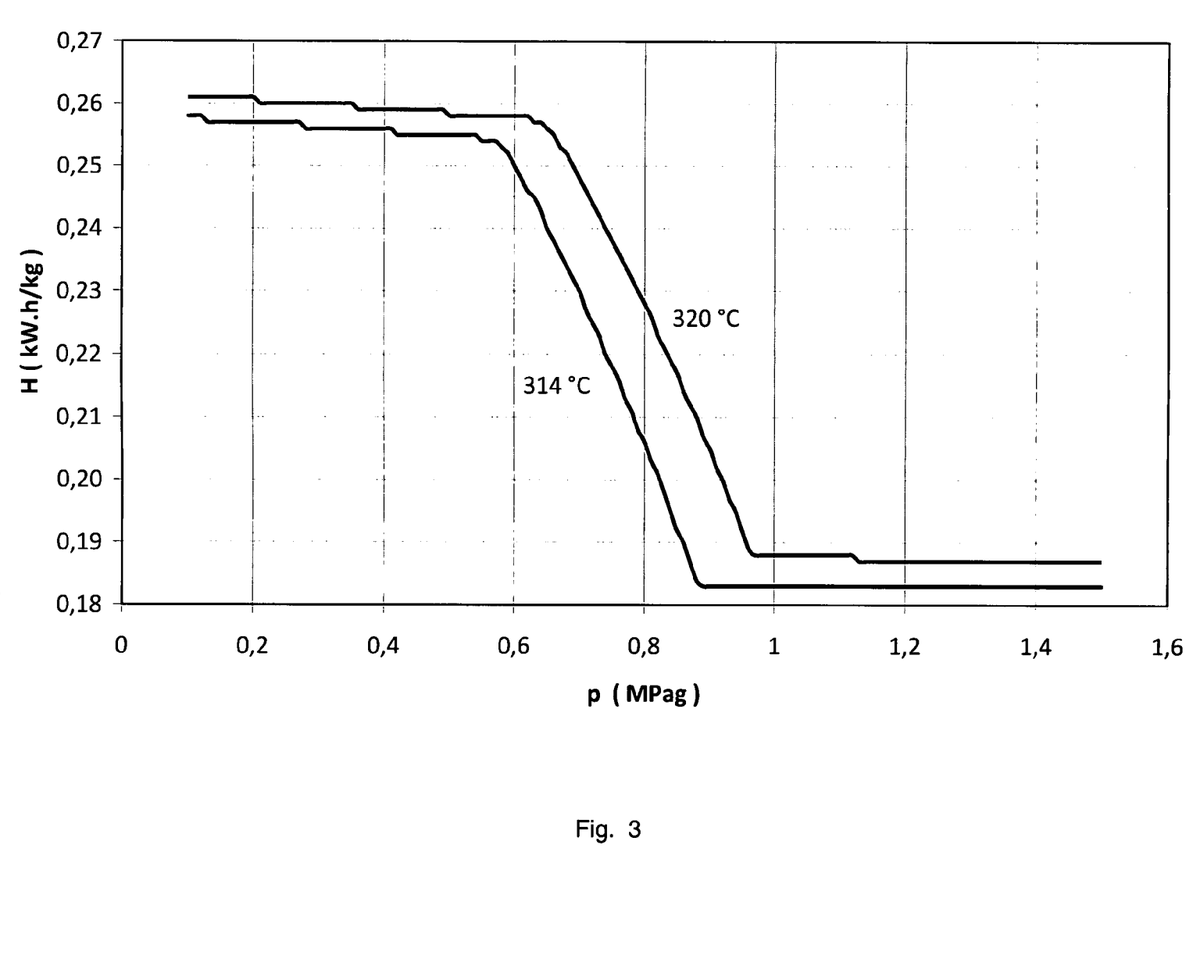
FIG. 3 is a graphical depiction of the relation between stream enthalpy (H) and pressure (p) for mixed aromatics streams at two temperatures.
Figure 4:
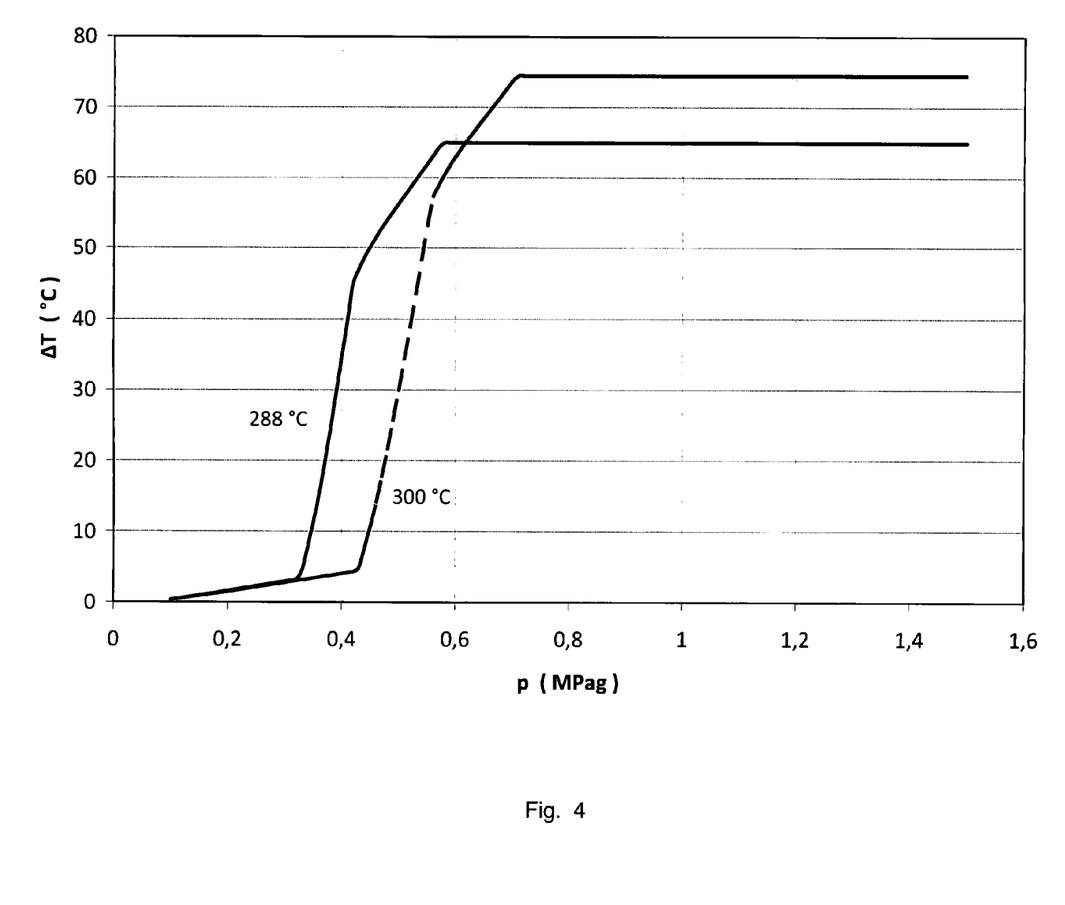
FIG. 4 is a plot of temperature difference across the expansion valve (ΔT) of a stream at two conditions versus inlet pressure (p).
Figure 5:
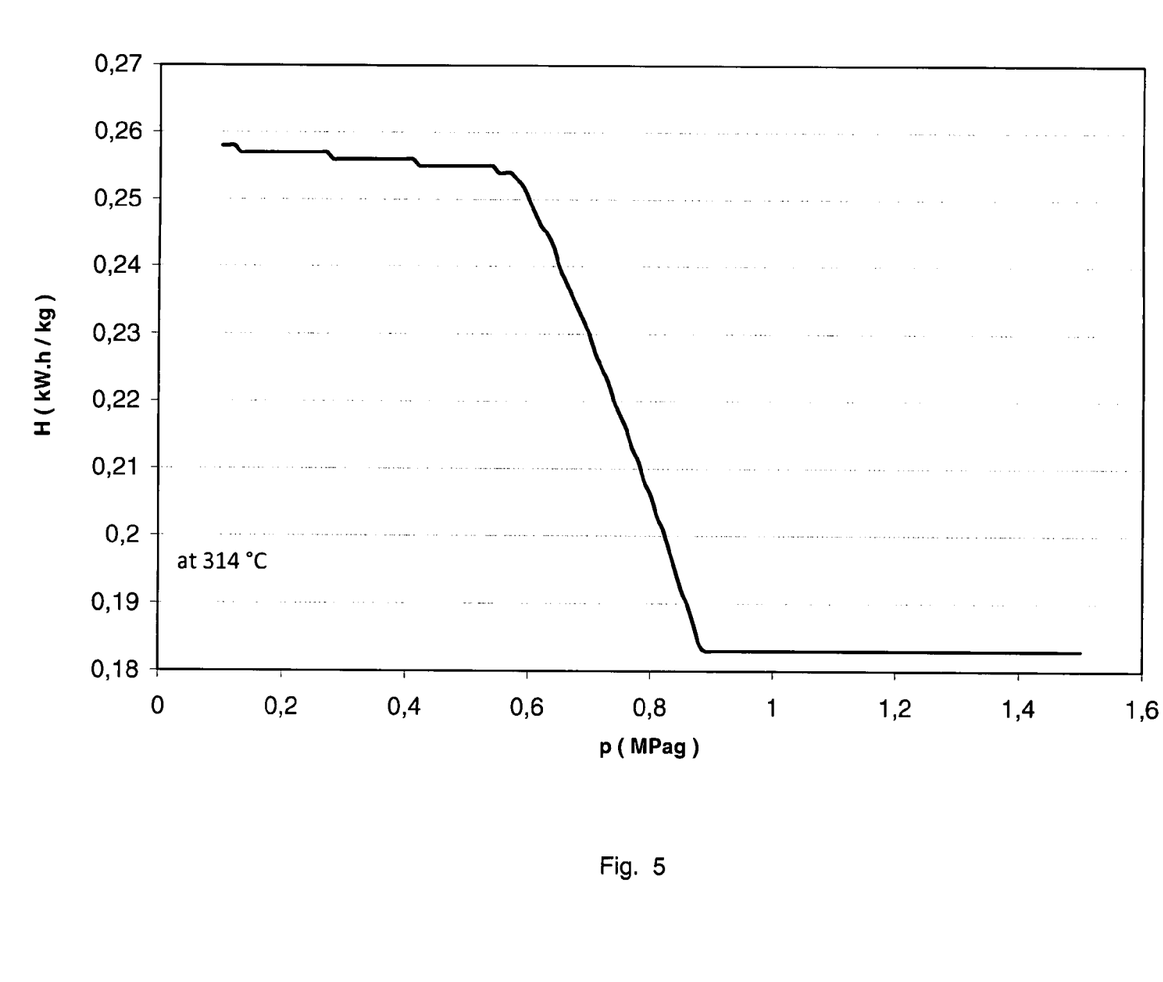
FIG. 5 is a plot of enthalpy (H) versus pressure for a heavy aromatics stream (at 314° C.).
Figure 6:
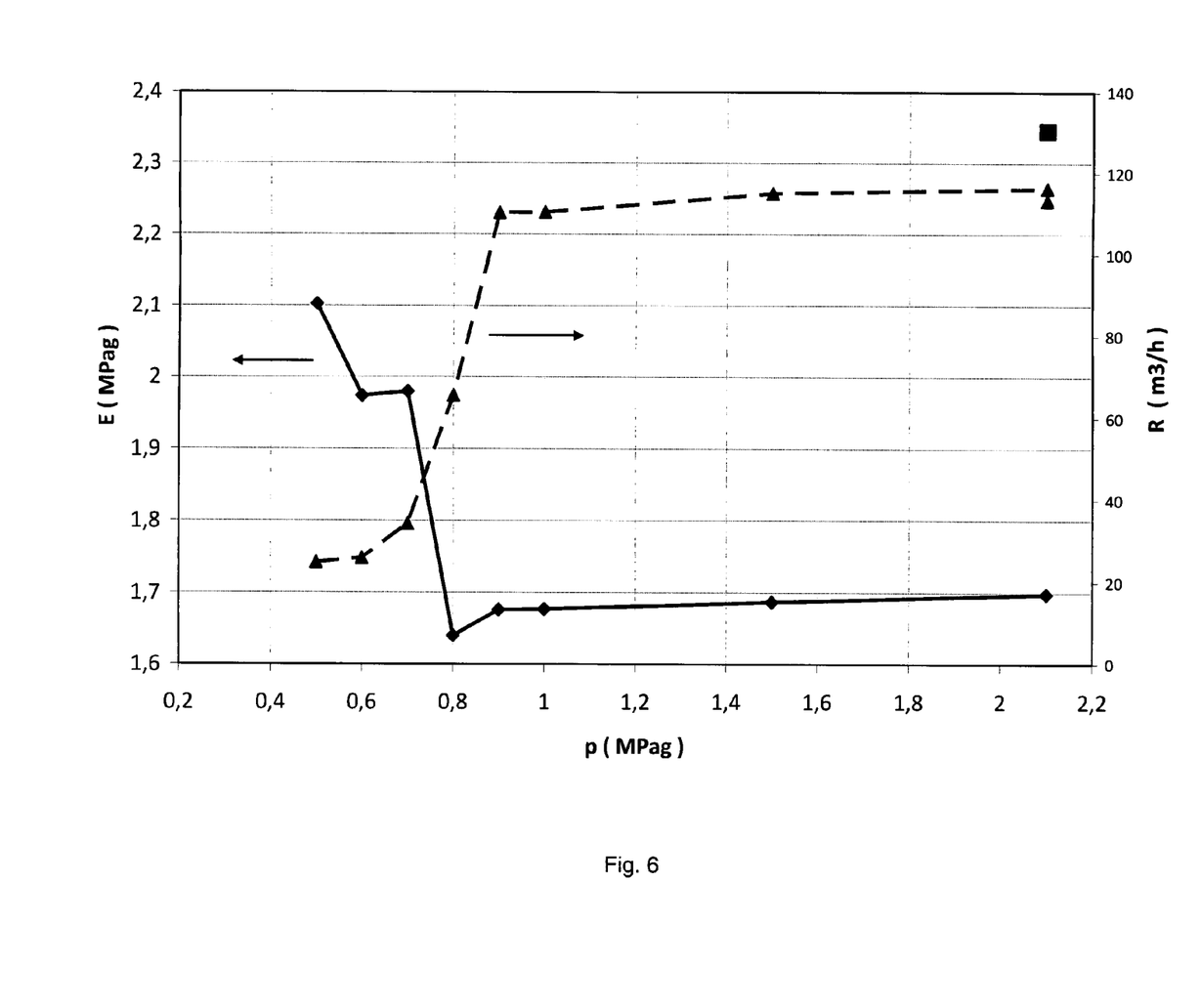
FIG. 6 is a graphical illustration of variation of both feed duty (E) and feed flow rate (R) with the stream pressure.

The above discussed processes are further illustrated in FIGS. 1 and 2, providing simplified process flow diagrams of 2 embodiments of the process according to the invention. In these figures, the last two digits of the reference numbers have the same or similar meaning where possible; as further elucidated in the descriptions below. FIG. 3 depicts the relation between stream enthalpy (H) and pressure (p) for mixed aromatics streams at two temperatures. FIG. 4 is a plot of temperature difference across th expansion valve (ΔT) of a stream at two conditions versus inlet pressure (p). FIG. 5 shows a plot of enthalpy H versus pressure for a heavy aromatics stream (at 314° C.). FIG. 6 shows variation of both feed duty (E) and feed flow rate (R) with the stream pressure.

In FIG. 1 a two-column distillation process is schematically depicted, wherein the upper parts of the columns are not shown for simplicity reasons. First and second columns 110 and 120 each have an integrated reboiler system 140 and 150, respectively. Feed enters the first column—indicated by an unnumbered arrow—and is separated into a first bottom product leaving the column via 111. The stream is split into streams 116 and 112. Part of the stream (112) is heated in fired reboiler 140 and recycled back to the column as heated stream 113 (first circulating reboiler stream). The operating pressure and temperature of column 110 is typically higher than the operating pressure and temperature of downstream column 120. The pressure of bottom product stream 116 can be optimized by pump or letdown pressure valve 170 producing stream 117. The temperature of product stream 117 can be adjusted by a slip stream 114 coming from the fired reboiler 140 after adjusting its pressure to that of 117. Depending on the required pressure and temperature of stream 117, either of streams 116 or 114 can be used alone or together. Stream 117 enters heat-exchange reboiler 150 of second column 120, now functioning as utility stream. The resulting heat-exchanged stream 134 is split into two streams. The first stream 133 is used as feed stream 136 for second column 120 after passing through expansion valve 180, to lower pressure and temperature to levels required for its further separation in column 120. In this scheme, stream 136 meets the column design capacity such that no other feed is needed; and second stream 135 representing any excess is returned upstream to the first reboiler 140. Column 120 produces a second bottom product 121, and part of this product is directed to the second reboiler 150, where it is heated against the hotter stream 117 (i.e. the utility stream). The heated product stream 122 is recycled back to the second column bottom to provide heat to the column separation process (second circulating reboiler stream). The remainder bottom product stream 125 may be further processed, for example in a third distillation column.

In FIG. 2 a similar two-column distillation process is schematically depicted, but with some modifications. In this case first bottom product leaving the column via 211 is divided into two streams 212 and 216. Stream 212 enters fired reboiler 240 using a separate heater coil producing stream 213 with pressure and temperature adequate for column 210 condition, which is recycled back to the column (first circulating reboiler stream). Stream 216 is first passed through pump or letdown pressure valve 270 to optimize its pressure (according to the requirement for stream 217) and then enters the fired heater 240 through a separate heating coil to adjust its temperature independently from stream 213 for downstream operation. Stream 217 then enters heat-exchange reboiler 250 of second column 120, now functioning as utility stream. The heat-exchanged stream 234 is split into two streams. The first stream 233 is subsequently used as feed stream 236 for second column 220 after passing through expansion valve 280, to lower pressure and temperature to levels required for its separation in column 220. Stream 236 meets the column design capacity in this embodiment; second stream 235 representing any excess is returned upstream to first reboiler 240. Column 220 produces a second bottom product 221, and part of this product is directed to the second reboiler 250, where it is heated against the hotter stream 116 (i.e. the utility stream). The heated product stream 222 is recycled back to the second column bottom to provide heat to the column separation process (second circulating reboiler stream). The remainder bottom product stream 225 may be further processed, if desired in a third distillation column.

Processing parameters and conditions of the process according to the invention are dependent on the composition of the feed stream to be separated and on the boiling points of the components therein. For a given feed mixture, the skilled person can define an initial set of conditions based on general knowledge, and the description and experiments of this application. Further optimisation can be performed based on simulations or some experiments.

For separation of a mixture of aromatic compounds comprising components with 8 or more carbon atoms, typical temperature and pressure ranges are 225-320° C. and 0.07-1 MPag (especially for the xylene and heavy aromatics columns)

The invention also relates to a distillation system comprising a first distillation column having a first fired reboiler, and at least a second distillation column having a second heat-exchange reboiler, a pump or letdown pressure valve to adjust the pressure of the first bottom product, and means to adiabatically adjust pressure and temperature of a stream coming from the second reboiler for using as feed for the second column; which system is suitable for separating a multi-component mixture in a process of the invention as described above.

Further, the invention relates in preferred embodiments to distillation systems as described in the above described preferred ways of operating the process of the invention.

The invention will now be further elucidated with the following non-limiting experiments.

Comparative Experiment 1 (Comp Exp 1)

In an industrially operated plant for making aromatics including benzene, toluene and xylenes (BTX), a two-column distillation system is comprised for xylene separation. The first column produces xylenes as top product for further separation, and a bottom product of mainly C9+ aromatics. The column bottom is heated by passing part of the C9+ aromatics stream through a fired reboiler and returning the hot stream to the column bottom at a pressure of 1 MPag. The other part of the C9+ aromatics product stream is sent downstream at a pressure of 2.1 MPag—as indicated in Table 1—as feed for a second column for separating into a C9 and C10 mono-aromatics top product, and C10+di-aromatics (eg naphthalenes) as bottom product. The overhead is sent to a plant upstream for reprocessing. The feed for the second column passes through a small heat exchanger and letdown pressure valve to reduce its temperature and pressure before entering the column. The second column reboiler is heated on the utility side by a second stream (as in traditional distillation) from first (xylene) column bottom product coming from the upstream of the first reboiler at 2.1 MPag, which was pressurized with a pump. The outlet flow from the second reboiler is returned upstream of the fired reboiler of first column. Some processing data is listed in Table 1. The capacity required to reheat the utility stream back to 314° C. is 2.02, and the cooling duty required to cool the feed stream to 225° C. is 0.32 MW, making a total of 2.34 MW used for heating and cooling of feeds.

Example 2 (Ex 2)

The installation as used in Comp. exp 1 was modified such that the original feed flow to the second column was stopped completely, and the feed heat exchanger was eliminated.

Instead, the second column feed was taken as part of the second reboiler outlet stream (i.e. from the utility stream), and passed through an expansion valve to regulate its pressure and reduce its temperature further before entering the second column as its feed. The excess stream from the second reboiler was fed upstream of the first fired heater of the first (xylene) column. This case is thus similar to the scheme shown in FIG. 1; using a pump but without a stream 114 from the first reboiler. The distillation operating parameters after above changes according to the current invention are shown in Table 1.

These results clearly show that for Example 2 the calculated fired reboiler energy duty, required to reheat the excess second reboiler return stream to its original temperature (i.e. 314° C.), decreased by 0.33 MW, or about 16%, and added to that the saving in feed cooling duty makes an overall decrease of 0.65 MW or 28% as a result of the heat-integration. The column worked satisfactory and under stable conditions during several months, with similar separation efficiencies.

In FIG. 3 the relation between stream enthalpy (H) and pressure (p) for two streams with the same C9+ mixed aromatics composition at two temperatures is shown; as calculated using software available on the market. Lowering the pressure at constant temperature and flow rate causes an increase in enthalpy below a certain pressure level, which is a function of the stream composition. Increasing the stream temperature shifts enthalpy change with pressure to higher values. The observed increase is due to the formation of a vapor phase at lower pressure and hence a gradual increase in enthalpy, and gives an operating window for the current invention. It is worth noting that keeping the temperature constant while decreasing the pressure in the range of enthalpy change in practice requires additional heating, which must be taken into consideration in the final heat balance.

Column duty is defined as [enthalpy of utility stream× stream flow rate]. Therefore, by operating in the variable enthalpy range one can use different flow rates by varying upstream pressure of the reboiler while keeping the column duty constant. The enthalpy variable range can be controlled as shown in FIG. 3 by varying the stream inlet temperature. Therefore it is possible not only to meet the required column energy duty, but to match the flow rate required as column feed as well.

For a liquid stream containing C9+ aromatics, the change in temperature ΔT before and after an expansion valve due to the pressure drop across it can be calculated using commercially available software. FIG. 4 is a plot of temperature difference of a stream at two constant inlet temperatures (288 and 300° C.) and a fixed outlet pressure of 0.07 MPag against a variable inlet pressure (p) of that stream. As shown a cooling effect to the liquid downstream of the valve is maintained by the constant ΔT with the upstream pressure up to a certain pressure level, below which a decrease in temperature drop occurs as the upstream pressure approaches the downstream pressure. The level of ΔT therefore varies with the temperature and pressure upstream of the expansion valve.

Example 3 (Ex 3)

Referring to FIG. 3, it can be seen that although the inlet pressure of 2.1 MPag lies in the flat region of enthalpy change for the stream with temperature 314° C., it is possible—see Example 2—to save energy in the heat duty and also improve the separation efficiency of the column by using the reboiler outlet stream as column feed with the use of an expansion valve downstream to cool down the feed further and adjust its pressure before entering the column. The figure also indicates further improvements can be made, e.g by minimizing the return reboiler stream back to the upstream fired reboiler. Example 3 represents results of a simulation based on Example 2, and using commercially available software. In Ex. 3 stream pressure was lowered to below xylene column bottom pressure, which can be done in practice using a let-down pressure valve with an additional heating to the original feed inlet temperature (as depicted in FIG. 1 configuration using stream 114 or as depicted in FIG. 2 configuration using stream 214).

For the situation of Ex. 3, FIG. 5 shows the operating window for making changes in pressure (p) with enthalpy per unit mass of feed (H), allowing calculation of required flow rate to meet the column duty and feed flow rate at stream temperature of 314° C. It also indicates pressure is preferably between 0.4 and 0.9 MPag, where there is potential to vary flow rate while meeting the same duty. Table 1 shows that the original pressurized hot stream is cooled twice, once in the second reboiler after exchanging heat with the column bottom liquid and once across the expansion valve. This is shown by the difference in temperatures between the feed to a reboiler at 314° C. and the inlet temperature to the expansion valve at 304° C. A further drop to 228° C. across the expansion valve can be achieved, totalling a drop of 86° C., which is about 30% reduction in original stream temperature and is adequate as a feed temperature for this column.

FIG. 6 shows the variation of both feed duty (E) and feed flow rate (R) with the stream pressure (p), at a constant column feed flow of 18 m³/h. The duty decreases with decreasing pressure from 2.1 to 0.8 MPag while the flow rate required for the boiler decreases. At lower pressures than 0.8 MPag the duty increases again as the stream requires additional heating due to formation of vapour phase as mentioned above, which was accounted for the calculation. As can be seen, the variation of flow rate is large between 0.6-0.9 MPag and can therefore be flexible to meet different column capacity. The duty required to meet the same column capacity but without integration as in Comp. Exp. 1 is also shown by a square (■).

The simulation results are shown in Table 1. By using an inlet pressure of 0.8 MPag and a temperature of 314° C. for the utility stream to the second reboiler in Ex. 3, it was possible to considerably reduce the return reboiler stream flow rate; i.e. to 65 m³/h. This results in higher energy savings than in Ex. 2; and in 19% reduction in heating duty of reboiler return stream compared to Comp. Exp. 1. In this case, the required duty for reheating the feed to 314° C. after lowering its pressure from 1 to 0.8 MPag is accounted for. In addition a further saving on cooling the feed without a heat exchanger is made, enabling a total energy saving of 30%.

Example 4 (Ex 4) and Comparative Example 5 (Comp Exp 5)

The feed flow rate to the column has been changed from 18 to 25 m³/h in this example using simulation (see Table 1), which illustrates that feed to the column can be flexible while maintaining energy saving by heat integration. The total heating duty for feed conditioning with no heat integration at this feed flow would in this case be 2.02 MW (listed in Table 1 as Comparative example 5). Heat integration in this case allows thus a saving of 58%.

TABLE 1

| Process parameter | Unit | Comp. exp. 1 | Ex 2 | Ex 3 | Ex 4 | Comp exp. 5 |
|---|---|---|---|---|---|---|
| First column | | | | | | |
| bottom product temperature | °C. | 314 | 314 | 314 | 314 | 314 |
| bottom product pressure | MPag | 1.0 | 1.0 | 1.0 | 1 | 1 |
| Bottom product pressure after adjustment | MPag | 2.1 | 2.1 | 0.8 | 0.8 | 2.1 |
| Second column | | | | | | |
| Feed temperature before/after heat-exchanger | °C. | 314/225 | | | | 314/225 |
| Reboiler inlet/outlet temperature | °C. | 314/287 | 314/289 | 314/304 | 314/287 | 314/278 |
| Feed temperature before/after expansion valve | °C. | | 289/225 | 304/228 | 287/224 | |
| Feed pressure | MPag | 0.07 | 0.07 | 0.07 | 0.07 | 0.07 |
| Feed flow rate | m³/h | 18 | 18 | 18 | 25 | 25 |
| Reflux temperature | °C. | 105 | 105 | 105 | 105 | 105 |
| Bottom temperature | °C. | 256 | 257 | 256 | 253 | 253 |
| Condenser energy duty | MW | −3.34 | −3.34 | −3.34 | −3.34 | −3.34 |
| Reboiler utility side feed flow rate | m³/h | 113 | 120 | 65 | 40 | 65 |
| Reboiler outlet flow rate to first reboiler | m³/h | 113 | 102 | 47 | 15 | 65 |
| Reboiler energy duty | MW | 2.11 | 2.09 | 1.91 | 1.63 | 1.62 |
| Feed heat exchanger duty | MW | 0.32 | — | — | — | 0.45 |
| First fired reboiler energy duty | MW | 2.02 | 1.69 | 1.64 | 0.85 | 1.57 |
| Total energy duty for feed conditioning | MW | 2.34 | 1.69 | 1.64 | 0.85 | 2.02 |

The invention claimed is:

1. A process for separating a multi-component feed mixture in a distillation system comprising a first distillation column having a first fired reboiler, and a second distillation column having a second heat-exchange reboiler, comprising:
    a) introducing the feed mixture to the first distillation column, and separating into at least a first top and a first bottom product;
    b) taking part of the first bottom product for providing heat to the second heat exchange reboiler as a utility stream;
    c) feeding part of said utility stream after heat-exchange as main feed to the second distillation column for further separation,
    wherein temperature and pressure of said part of said utility stream are adiabatically adjusted before feeding to the second column.

2. The process according to claim 1, further comprising d) feeding the other part of said utility stream after heat-exchange to the first reboiler.

3. The process according to claim 1, wherein in step c) said part of the utility stream is the single feed stream to the second column.

4. The process according to claim 1, further comprising, in step b), adjusting pressure of the first bottom product; and
    d) combining another part of said utility stream after heat-exchange with another part of the first bottom product, heating in the first fired reboiler and returning to the first distillation column as a first circulating reboiler stream.

5. The process claim 4, wherein part of the heated stream from the first fired reboiler of step d) is added to the utility stream in step b) to adjust temperature of said utility stream before providing heat to the second heat exchange reboiler.

6. The process according to claim 1, wherein the feed mixture comprises hydrocarbons with boiling points higher than 145° C.

7. The process according to claim 1, wherein the feed mixture comprises aromatic hydrocarbons with 8 or more carbon atoms.

8. The process according to claim 1, wherein temperature and pressure of said part of said utility stream are adiabatically adjusted via an expansion valve.

9. The process according to claim 1, further comprising taking part of a second bottom product, heating in the second heat-exchange reboiler and returning to the second distillation column as a second circulating reboiler stream.

10. A process for separating a multi-component feed mixture in a distillation system comprising a first distillation column having a first fired reboiler, and a second distillation column having a second heat-exchange reboiler, comprising:
    a) introducing the feed mixture into the first distillation column, and separating into at least a first top and a first bottom product;
    b) adjusting pressure of the first bottom product and heating in the first fired reboiler and returning part thereof to the first distillation column as a first circulating reboiler stream;
    c) taking another part of heated stream from the first fired reboiler for providing heat to the second heat-exchange reboiler as a utility stream,
    d) feeding part of said utility stream after heat-exchange as main feed to the second distillation column for further separation; and
    e) heating another part of said utility stream after heat-exchange with the first bottom product in step b);
    wherein temperature and pressure of said part of said utility stream are adiabatically adjusted before feeding to the second column.

11. The process according to claim 10, further comprising feeding the another part of said utility stream after heat-exchange to the first reboiler.

12. The process according to claim 10, further comprising taking part of a second bottom product, heating in the second heat-exchange reboiler and returning to the second distillation column as a second circulating reboiler stream.

13. A distillation system, comprising: a first distillation column having a first fired reboiler, and a second distillation column having a second heat-exchange reboiler, wherein the first distillation column is in fluid communication with the second distillation column, and wherein the pressure and temperature of a stream coming from the second heat-exchange reboiler for using as feed for the second distillation column is adjustable adiabatically via an expansion valve.

14. The distillation system according to claim 13, wherein the pressure of a first bottom product is adjustable via a letdown pressure valve.

* * * * *